United States Patent
Sachar et al.

(10) Patent No.: US 10,849,730 B2
(45) Date of Patent: *Dec. 1, 2020

(54) THERAPEUTIC AGENT COATED ANGIOPLASTY BALLOON WITH EMBOLIC FILTER AND PROTECTIVE COVER

(71) Applicant: Contego Medical, Inc., Raleigh, NC (US)

(72) Inventors: Ravish Sachar, Raleigh, NC (US); Eugene Serina, San Jose, CA (US); Dave Stern, Grayson, GA (US)

(73) Assignee: Contego Medical, Inc., Raleigh, NC (US)

( * ) Notice: Subject to any disclaimer, the term of this patent is extended or adjusted under 35 U.S.C. 154(b) by 195 days.

This patent is subject to a terminal disclaimer.

(21) Appl. No.: 15/840,294

(22) Filed: Dec. 13, 2017

(65) Prior Publication Data

US 2018/0161143 A1    Jun. 14, 2018

Related U.S. Application Data

(60) Provisional application No. 62/433,521, filed on Dec. 13, 2016.

(51) Int. Cl.
*A61F 2/01* (2006.01)
*A61M 25/10* (2013.01)
(Continued)

(52) U.S. Cl.
CPC .............. *A61F 2/013* (2013.01); *A61L 29/08* (2013.01); *A61L 29/14* (2013.01); *A61L 29/16* (2013.01);
(Continued)

(58) Field of Classification Search
CPC ........ A61F 2/013; A61F 25/10; A61F 25/104; A61F 25/0026; A61F 2002/011;
(Continued)

(56) References Cited

U.S. PATENT DOCUMENTS 4,655,771 A     4/1987  Wallsten et al.
5,843,027 A  *  12/1998 Stone ...................... A61F 2/958
                                                           604/509
(Continued)

FOREIGN PATENT DOCUMENTS

CN      102227194 A    10/2011
WO    2010042458 A1     4/2010
(Continued)

OTHER PUBLICATIONS

Office Action Issued by the Chinese National Intellectual Property Administration in Chinese Patent Application No. 201680069353.4 dated Jun. 19, 2019. 16 pages, including English translation.
(Continued)

*Primary Examiner* — Scott J Medway
*Assistant Examiner* — Dung T Ulsh
(74) *Attorney, Agent, or Firm* — Meunier Carlin & Curfman LLC (57)    ABSTRACT

Various implementations of a percutaneous transluminal angioplasty device include a catheter, a filter, and an expandable balloon. The filter is coupled adjacent a distal end of the catheter and is movable between an unexpanded and expanded configuration via a filter activation wire extending through a lumen of the catheter. An anti-stenotic therapeutic agent is disposed on an outer surface of the balloon, and the balloon is disposed on the catheter proximally of the filter. An axial movable sheath is positioned over the balloon and filter during deployment to a target site and is axially retracted away from the filter and balloon prior to treatment of a lesion. At the target site, the exposed filter is expanded via the filter activation wire. Then, the exposed balloon is inflated to dilate and deliver the therapeutic agent to the lesion.

29 Claims, 9 Drawing Sheets

(51) Int. Cl.
*A61L 29/08* (2006.01)
*A61L 29/16* (2006.01)
*A61L 29/14* (2006.01)
*A61M 25/00* (2006.01)

(52) U.S. Cl.
CPC .......... *A61M 25/10* (2013.01); *A61M 25/104* (2013.01); *A61F 2/011* (2020.05); *A61F 2002/016* (2013.01); *A61F 2230/0004* (2013.01); *A61F 2230/0076* (2013.01); *A61L 2300/416* (2013.01); *A61M 25/0026* (2013.01); *A61M 2025/105* (2013.01); *A61M 2025/1081* (2013.01)

(58) Field of Classification Search
CPC .......... A61F 2002/016; A61F 2002/015; A61F 2002/30092; A61F 2002/91525; A61F 2002/91575; A61F 2002/91508; A61F 2002/91516; A61F 2002/9155; A61F 2230/0067; A61F 2230/0008; A61F 2230/005; A61F 2230/0076; A61F 2230/0054; A61F 2/958; A61F 2/01; A61F 2/915; A61F 2/82; A61F 2/95; A61F 2/2427; A61F 2/2433; A61F 2/2445; A61F 2/2451; A61F 2210/0014; A61F 2250/0067; A61M 25/104; A61M 25/1011; A61M 2025/0004; A61B 2017/2212; A61B 2017/00539; A61B 2017/22049; A61B 17/221; A61B 17/00234

See application file for complete search history.

(56) References Cited

U.S. PATENT DOCUMENTS

| | | | |
|---|---|---|---|
| 6,254,611 B1 | 7/2001 | Vrba | |
| 6,391,050 B1* | 5/2002 | Broome | A61F 2/966 |
| | | | 623/1.11 |
| 6,569,193 B1 | 5/2003 | Stalker et al. | |
| 6,511,503 B1 | 6/2003 | Burkett et al. | |
| 6,669,723 B2 | 12/2003 | Killion et al. | |
| 6,736,840 B2 | 5/2004 | Fischell et al. | |
| 8,758,424 B2 | 6/2014 | Sachar et al. | |
| 2002/0016564 A1 | 2/2002 | Courtney et al. | |
| 2003/0004535 A1 | 1/2003 | Musbach et al. | |
| 2003/0055480 A1 | 3/2003 | Fischell et al. | |
| 2003/0167084 A1 | 9/2003 | Orlowski et al. | |
| 2004/0220607 A1 | 11/2004 | Donovan et al. | |
| 2004/0230284 A1 | 11/2004 | Headley et al. | |
| 2005/0004594 A1 | 1/2005 | Nool et al. | |
| 2005/0038468 A1 | 2/2005 | Panetta et al. | |
| 2005/0149166 A1 | 7/2005 | Schaeffer et al. | |
| 2005/0228438 A1* | 10/2005 | Sachar | A61F 2/013 |
| | | | 606/200 |
| 2007/0156168 A1 | 7/2007 | Dunfee et al. | |
| 2007/0173929 A1 | 7/2007 | Boucher et al. | |
| 2007/0185559 A1 | 8/2007 | Shelso et al. | |
| 2008/0077223 A1 | 3/2008 | Fischell et al. | |
| 2008/0269868 A1* | 10/2008 | Bei | A61F 2/958 |
| | | | 623/1.11 |
| 2009/0105686 A1 | 4/2009 | Snow et al. | |
| 2009/0192584 A1 | 7/2009 | Gerdts et al. | |
| 2010/0036481 A1 | 2/2010 | Dubrul et al. | |
| 2010/0268263 A1 | 10/2010 | Edelman et al. | |
| 2012/0041469 A1 | 2/2012 | Fischell et al. | |
| 2012/0277843 A1 | 11/2012 | Weber et al. | |
| 2012/0330346 A1 | 12/2012 | Frimerman et al. | |
| 2013/0261722 A1* | 10/2013 | Hossainy | A61F 2/00 |
| | | | 623/1.11 |
| 2014/0142598 A1 | 5/2014 | Fulton et al. | |
| 2014/0214067 A1 | 7/2014 | Sachar et al. | |
| 2015/0051688 A1 | 2/2015 | Cummins | |
| 2015/0133918 A1 | 5/2015 | Sachar | |
| 2015/0306361 A1 | 10/2015 | Feig et al. | |
| 2016/0089228 A1 | 3/2016 | Sachar et al. | |
| 2016/0213458 A1* | 7/2016 | Sachar | A61F 2/013 |

FOREIGN PATENT DOCUMENTS

| | | |
|---|---|---|
| WO | 2014/085590 A1 | 6/2014 |
| WO | 2017075273 | 5/2017 |

OTHER PUBLICATIONS

International Preliminary Report on Patentability issued by the International Bureau in International Application No. PCT/US2017/066067 dated Jun. 27, 2019. 8 pages.

Notice of Allowance issued in U.S. Appl. No. 15/336,242, dated Feb. 23, 2018.

International Search Report and Written Opinion issued in International Application No. PCT/US2017/66067, dated Mar. 5, 2018.

Office Action issued for U.S. Appl. No. 15/336,242, dated Mar. 30, 2017.

Office Action issued for U.S. Appl. No. 15/336,242, dated Sep. 29, 2017.

Advisory Action issued for U.S. Appl. No. 15/336,242, dated Dec. 28, 2017.

International Search Report and Written Opinion issued for International Application No. PCT/US2016/059203, dated Feb. 20, 2017.

International Preliminary Report on Patentability conducted in International Application No. PCT/US2016/059203, dated May 11, 2018.

Extended European Search Report, issued by the European Patent Office in Application No. EP 17880585.9 dated Jun. 22, 2020. 7 pages.

* cited by examiner

THERAPEUTIC AGENT COATED ANGIOPLASTY BALLOON WITH EMBOLIC FILTER AND PROTECTIVE COVER

CROSS REFERENCE TO RELATED APPLICATIONS

This application claims the benefit of U.S. Provisional Application No. 62/433,521, filed Dec. 13, 2016, which is incorporated by reference in its entirety for all purposes.

BACKGROUND

Angioplasty catheters are used in catheter-based procedures to open up a blocked vessel and restore blood flow. In general, physicians use separate devices to perform a single procedure. That is, when treating a vascular stenosis, separate devices/tools are used for embolic protection and balloon dilatation. The use of multiple devices to complete a single procedure has many drawbacks. For example, exchanging devices leads to longer procedure time, which poses patient safety risks; manipulation of multiple devices poses potential clinical risk; and interaction between multiple devices poses a risk of device failure. Thus, it is necessary for the physician to be trained on multiple devices, and there are higher costs to use multiple devices separately.

For treatment of atherosclerotic lesions in the arteries of the lower extremities, physicians use angioplasty catheters in which the exterior of the balloon element has been coated with an pharmaceutical that is designed to inhibit regrowth of tissue following treatment. One problem, however, with drug coated balloons is that the drug coating material may fragment off the balloon while it is being expanded within the treatment site resulting in a bolus of embolic particles carried along the artery toward more distal anatomy. Since the arteries of the legs decrease in diameter as the blood flows toward the feet, these smaller arteries are more likely to become blocked as a result of this embolic flow. In addition, the accumulation of pharmaceuticals with antiproliferative properties in the lower extremities can cause various medical problems such as delayed wound healing.

A further problem is that the drug can begin to degrade off the balloon surface as soon as the catheter is introduced into the circulatory system. Thus, by the time the balloon has been positioned within the target lesion, the concentration of the drug on the balloon surface may be diluted so that it is insufficient to deliver the specified dosage to affect the desired inhibitory response. In addition to reducing the effectiveness of the drug treatment, the increased concentration of the pharmaceutical in the circulatory system may impart systemic toxicological effects.

To address this risk, many types of vascular embolic filters have been designed. These filters can be positioned within the artery past the lesion to be treated and remain in place during the entire procedure. However, this requires the use of a separate device, additional maneuvering within the artery, and added complexity of the procedure.

Accordingly, there is a need for a drug coated balloon angioplasty catheter for use within the arteries of the lower extremities that combines a distal protection filter into the same device and includes an exterior cover that isolates the coated balloon during introduction into the artery until the balloon is positioned within the target lesion in order to prevent premature delivery of the drug from the surface of the balloon.

SUMMARY

Various implementations include a percutaneous transluminal angioplasty device that includes a multi-lumen catheter, a filter, an expandable balloon coated with an anti-restenosis pharmaceutical coating. When deployed within the vasculature, the filter serves to catch any fragments that separate from the drug coated balloon during its expansion. Some implementations of the percutaneous transluminal device also include a moveable outer sheath that covers the coated balloon until the operator is ready to perform the dilatation procedure. The sheath serves to limit the protect the drug coating on the surface of the balloon from dilution or degradation as the balloon is delivered to the target lesion. The inclusion of each of these features as part of one device reduces the complexity, time, and risk associated with the procedure.

The multi-lumen catheter has a proximal end and a distal end. The catheter defines a first lumen, a second lumen, and a third lumen, and each lumen extends through at least a portion of the catheter. The filter is disposed adjacent the distal end of the catheter, and the filter is movable between unexpanded and expanded configuration. The expandable balloon is disposed between the filter and the distal end of the catheter. At least a portion of the expandable balloon is coated with an anti-restenosis therapeutic agent (e.g., a drug). In some embodiments, the device can also include a movable sheath that extends over the balloon and filter, and a sheath wire that is coupled to the movable sheath. The sheath wire extends through one of the lumens defined by the catheter, and movement of the sheath wire translates the sheath axially. The sheath wire is moved axially to translate the sheath axially, and the axial movement of the sheath wire translates the sheath in the same direction as the axial movement of the sheath wire.

In some implementations, the therapeutic agent is an anti-stenotic therapeutic agent, such as Sirolimus or Paclitaxel. However, in other implementations, the therapeutic agent comprises any therapeutic agent for delivery to an interior wall of a vessel.

In some implementations, the device further includes a filter activation wire that is disposed within a first lumen, and a distal end of the filter activation wire is coupled to the filter.

In some implementations, the filter includes a filter frame and a filter membrane. The filter frame has a distal end and a proximal end, and the proximal end of the filter frame is fixedly coupled to the catheter. The distal end of the filter frame is slidably coupled to the catheter. The filter membrane has a distal end and proximal end, and the distal end of the filter membrane is fixedly coupled to the catheter distally of the proximal end of the filter membrane and the distal end of the filter frame. The proximal end of the filter membrane is fixedly coupled to a portion of the filter frame. The distal end of the filter activation wire is coupled to the distal end of the filter frame, and tensioning the filter activation wire in a proximal direction urges the distal end of the filter frame in axial proximal direction from an unexpanded configuration to an expanded configuration.

In some implementations, the device includes a handle coupled to a proximal end of the catheter, and the handle is coupled to the filter activation wire and the sheath wire. For example, in some implementations, the handle includes a first actuator coupled to the filter activation wire and a second actuator coupled to the sheath wire. The first actuator is manipulatable to expand and contract the filter via the filter activation wire, and the second actuator is manipulatable to axially move the sheath.

In some implementations, the third lumen is a balloon inflation lumen, and the catheter further defines an inflation port between an external surface of the catheter and the third lumen.

In some implementations, the catheter defines a guidewire port, and the guidewire port has a first opening defined by one of the first, second, or third lumen and a second opening defined by an exterior surface of the catheter. The first opening of the guidewire port is disposed distally relative to the second opening. In a further implementation, a guide wire is disposed within at least a portion of the first, second, or third lumen that defines the first opening of the guidewire port.

In some implementations, at least a portion of the filter has a radius in the expanded configuration that corresponds to an inner diameter of a blood vessel into which the filter is disposed.

In some implementations, the catheter includes a proximal portion and a distal portion, and the proximal portion is disposed adjacent a proximal end of the catheter and the distal portion is disposed adjacent a distal end of the catheter. The proximal portion of the catheter defines a sheath wire lumen, a proximal filter activation wire lumen, and a proximal balloon inflation lumen. The distal portion of the catheter defines a guidewire lumen, a distal filter activation wire lumen, and a distal balloon inflation lumen. In further implementations, the proximal balloon inflation lumen and the distal balloon inflation lumen are axially aligned, the proximal filter activation wire lumen and the distal filter activation wire lumen are axially aligned, and/or the sheath wire lumen and the guidewire lumen are axially aligned.

Methods of treating arteries are also disclosed herein. The methods include routing a percutaneous transluminal angioplasty device through a body to a site of a vascular stenosis, disposing a distal end of a multi-lumen catheter downstream of the vascular stenosis such that the balloon is disposed radially inward of the vascular stenosis and the filter is disposed downstream of the vascular stenosis, deploying the filter downstream of the vascular stenosis, inflating the balloon to push the outer surface of the balloon against the vascular stenosis and deliver the therapeutic agent to the vascular stenosis, deflating the balloon, contracting the filter, and removing the catheter from the body. In implementations that include an axially movable sheath, prior to inflating the expandable balloon the sheath is moved proximally to expose either a portion of or the entirety of the expandable balloon. When only a portion of the expandable balloon is exposed, the exposed portion of the balloon is expanded to a greater diameter than the portion of the balloon remaining under the axially movable sheath.

The details of one or more embodiments of the disclosure are set forth in the accompanying drawings and the description below. Other features, objects, and advantages of the disclosure will be apparent from the description and drawings, and from the claims.

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

BRIEF DESCRIPTION OF DRAWINGS

Various implementations of a percutaneous transluminal angioplasty device are described in detail in the following drawings. The drawings are merely exemplary to illustrate the structure of devices and certain features that may be used singularly or in combination with other features. The invention should not be limited to the examples shown.

DETAILED DESCRIPTION

Certain terminology is used in the following description for convenience only and is not limiting. The words "right," "left," "lower," and "upper" designate direction in the drawings to which reference is made. The words "inner" and "outer" refer to directions toward and away from, respectively, the geometric center of the described feature or device. The words "distal" and "proximal" refer to directions taken in context of the item described and, with regard to the instruments herein described, are typically based on the perspective of the surgeon using such instruments. The terminology includes the above-listed words, derivatives thereof, and words of similar import.

Various implementations relate to percutaneous transluminal angioplasty devices suitable for use therewith.

Figure 1:
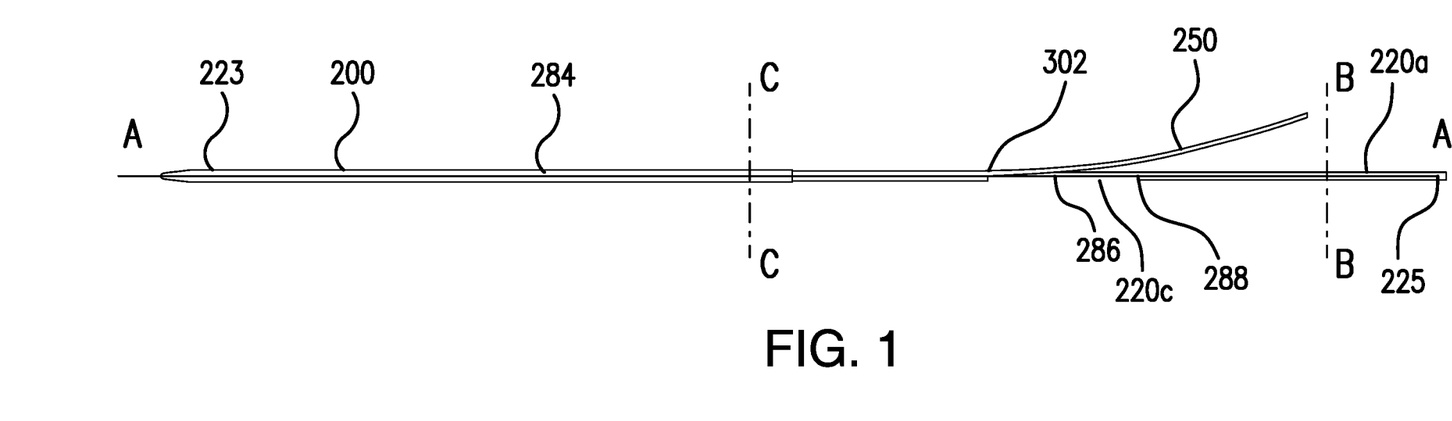
FIG. 1 is a side view of an exemplary percutaneous transluminal angioplasty device according to one implementation.
Figure 2:
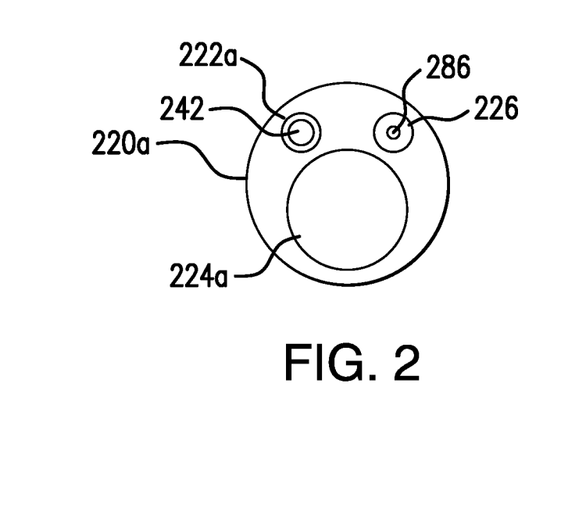
FIG. 2 is a cross sectional view of the percutaneous transluminal angioplasty device as taken through the B-B line of FIG. 1.
Figure 3:
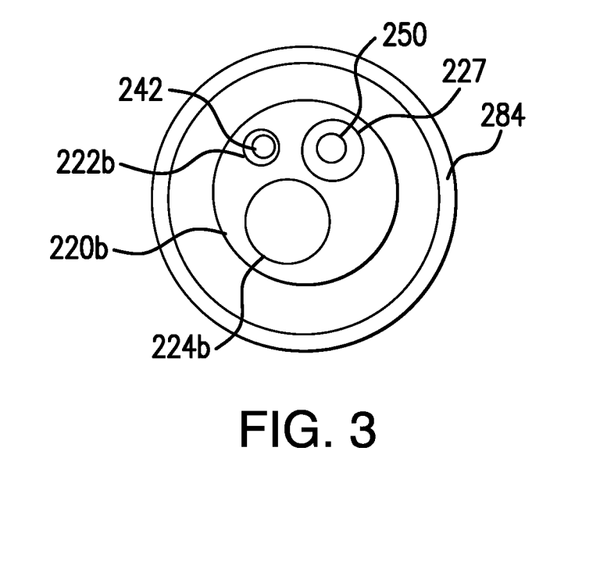
FIG. 3 is a cross sectional view of the percutaneous transluminal angioplasty device as taken through the C-C line of FIG. 1.
Figure 4:
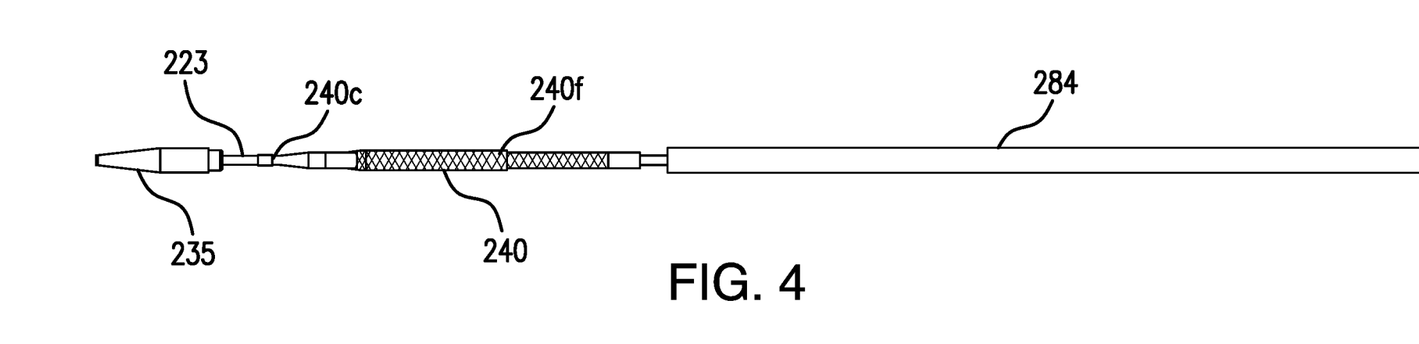
FIG. 4 is a side view of the percutaneous transluminal angioplasty device shown in FIG. 1 with the filter assembly exposed and unexpanded.
Figure 5:
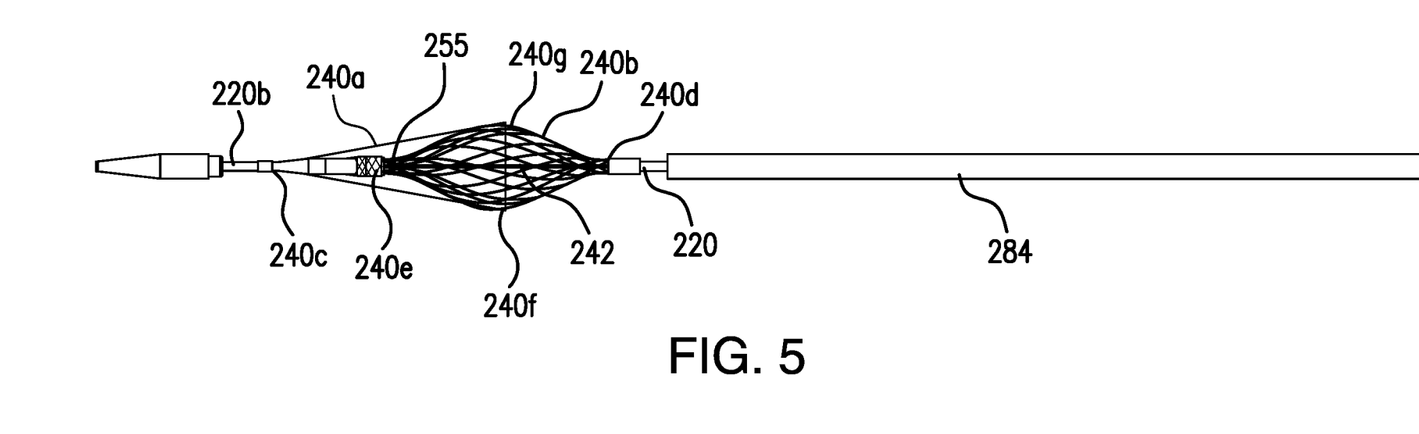
FIG. 5 is a side view of the percutaneous transluminal angioplasty device shown in FIG. 1 with the filter assembly expanded.

FIG. 1 is a side view of the percutaneous transluminal angioplasty device 200 with the sheath 284 covering the filter assembly 240 and balloon 260. FIGS. 2 and 3 illustrate cross sectional view of the device 200 as taken through the B-B and C-C lines, respectively. FIGS. 4 and 5 illustrate the configuration and operation of the device 200 as the filter assembly 240 is exposed and then deployed, respectively.

In the implementation shown in FIG. 1, the device 200 includes a catheter 220 having a proximal end 225 and a distal end 223. The catheter 220 includes a proximal portion 220a disposed adjacent the proximal end 225, a distal portion 220b disposed adjacent the distal end 223, and mid portion 220c. The proximal portion 220a and the distal portion 220b are coupled together at the mid portion 220c. For example, the proximal portion 220a and the distal portion 220b are integrally formed together at mid portion 220c according to some implementations. And, in other implementations, the portions 220a, 220b are formed separately and coupled together at mid portion 220c using thermal or chemical bonding mechanisms, for example. In other implementations, the catheter 220 includes one or more portions, and the number of portions depends at least in part on the control components to be provided by the device.

FIG. 2 illustrates a cross sectional view of the proximal portion 220a of the catheter 220 as taken through line B-B as shown in FIG. 1, and FIG. 3 illustrates a cross sectional view of the distal portion 220b of the catheter 220 as taken through line C-C as shown in FIG. 1, according to one implementation. The cross-sectional views in FIGS. 2 and 3 illustrate an exemplary arrangement of one or more lumens extending through at least a portion of the catheter 220. As shown in FIG. 2, the proximal portion 220a defines a proximal balloon inflation lumen 224a, a sheath wire lumen 226, and a proximal filter activation wire lumen 222a. And, as shown in FIG. 3, the distal portion 220b defines a distal balloon inflation lumen 224b, a distal filter activation wire lumen 222b, and a guidewire lumen 227. In some implementations, the proximal and distal balloon inflation lumens 224a, 224b are axially aligned, and in other implementations, the lumens 224a, 224b are in communication with each other but are not axially aligned. Similarly, in some implementations, the proximal and distal filter activation wire lumens 222a, 222b are axially aligned, and in other implementations, the lumens 222a, 222b are in communication with each other but are not axially aligned. And, in some implementations, the sheath wire lumen 226 is axially aligned with the guidewire lumen 227, and other implementations, the sheath wire lumen 226 and the guidewire lumen 227 are not axially aligned. Further, in some implementations, the sheath wire lumen 226 and the guidewire lumen 227 are in communication with each other, regardless of their axial alignment. In addition, in some implementations, distal ends of one or more of lumens 222a, 224a, 226 in the proximal portion 220a of the catheter 220 are axially spaced apart from proximal ends of one or more lumens 222b, 224b, 227 in the distal portion 220b of the catheter 220. And, in some implementations, the distal ends of one or more lumens 222a, 224a, 226 abut the proximal ends of one or more lumens 222b, 224b, 227 in the distal portion 220b of the catheter 220.

According to various implementations, the lumens are sized to accommodate various control components passing through the lumens, and the orientation, sizes, and/or number of lumens shown in FIGS. 2 and 3 is selected depending on the components to be controlled by the device 200. In addition, the control components described above in relation to FIG. 1 are exemplary, and, in other implementations, the device includes more or less control components and/or lumens, depending on the intended use of the device. Furthermore, the lumens described above in relation to FIG. 1 receive one control component each, but in other implementations, one or more lumens are sized to receive one or more control components.

As illustrated in FIGS. 4-5, the device 200 further includes a distal tip 235 coupled to the distal end 223. In the implementation shown in FIGS. 4-5, the distal tip 235 is conical or frusto-conically shaped to facilitate penetration through the body. The tip 235 defines a guidewire port through which a guidewire 250 extends during placement of the device 200 within the body. The tip 235 according to one implementation includes a low durometer material, such as PEBAX. However, in other implementations, the tip includes other suitable shapes (e.g., spherical or hemispherical, pyramidal, blunted) depending on the intended path of the tip through the body.

According to the implementation shown in FIGS. 4-5, the filter assembly 240 is coupled to the distal portion 220b of the catheter 220 adjacent the distal end 223 of the catheter 220 and is disposed axially proximal to the tip 235. Distal portion 220b extends axially through the filter assembly 240 (shown in FIG. 11). The filter assembly 240 is moveable between an expanded and unexpanded configuration. The filter assembly 240 in the unexpanded configuration, which is illustrated in FIG. 4, is sized and configured for insertion and passage through a blood vessel. In the expanded configuration, illustrated in FIG. 5, the filter assembly 240 is sized and configured to capture emboli within the bloodstream. For example, at least a portion of the filter assembly 240 in the expanded configuration extends across a diameter of the vessel to catch emboli that may be flowing through the bloodstream.

The filter assembly 240 includes a filter membrane 240a and a filter frame 240b. The filter membrane 240a is frusto-conically shape, and the filter frame 240b is egg shaped in the implementation shown in FIG. 5. A conical tip 240c of the membrane 240a is fixedly coupled around the distal portion 220b of the catheter 220, and a distal end 240e of the filter frame 240b is disposed proximally of the conical tip 240c of the membrane 240a and is slidably coupled around the distal portion 220b. A proximal portion 240f of the filter membrane 240a is fixedly coupled to a central portion 240g of the filter frame 240b, such as via thermal or chemical bonding or another suitable coupling mechanism. And, a proximal portion 240d of the filter frame 240b is fixedly coupled around the distal portion 220b. In other implementations, the shape of the membrane and/or filter frame may be different than shown in FIG. 5 and may be based at least in part on the anatomy in which the filter assembly is to be disposed.

Figure 11:
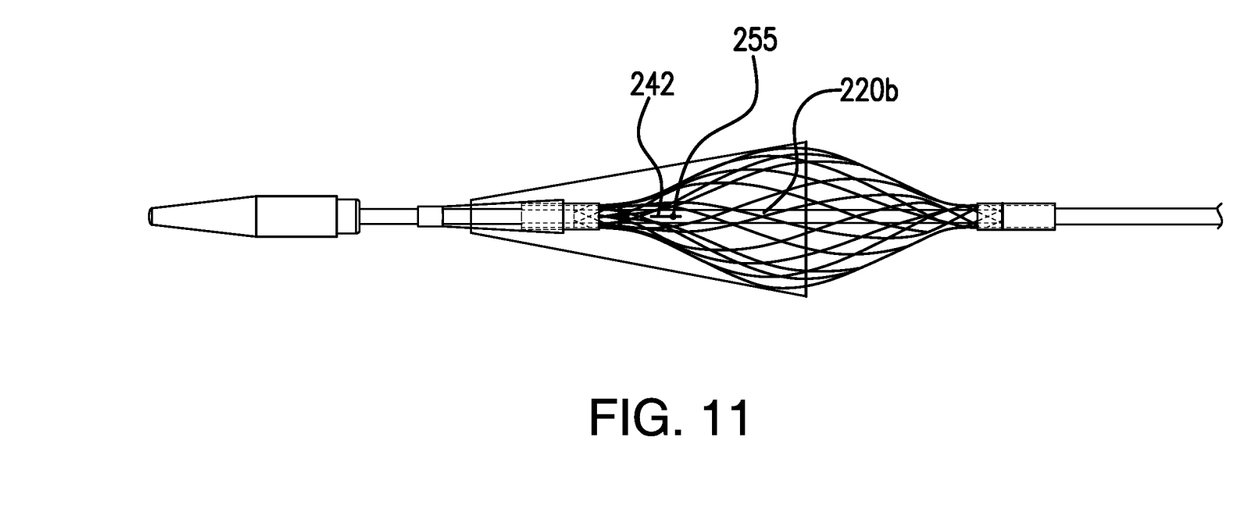
FIG. 11 is a side view of the percutaneous transluminal angioplasty device shown in FIG. 1, showing the catheter extending axially through the filter frame and the filter activation wire exiting the filter activation wire port.

As shown in FIGS. 2 and 3, and 11 a filter activation wire 242 extends through the filter activation wire lumens 222a, 222b, and a distal end of the filter activation wire 242 extends through a filter activation wire port 255 and is coupled to the distal end 240e of the filter frame 240b. The filter activation wire port 255 is defined by the distal portion 220b of the catheter 220. The filter activation wire port 255 has a first opening and a second opening. The first opening is defined by an external surface of the distal portion 220b of the catheter 220 and is disposed between the distal end 240e of the filter frame 240b and the proximal end 240d of the filter frame 240b. The second opening is defined by lumen 222b. In some implementations, the second opening of the port 255 is axially proximal the first opening, and in other implementations, the first and second openings of port 255 are radially aligned. The filter activation wire port 255 is distally disposed relative to the expandable balloon 260.

Tensioning the filter activation wire 242 in the proximal direction causes the distal end 240e of the filter frame 240b to move proximally, which causes the filter assembly 240 to move from the unexpanded configuration to the expanded configuration. Similarly, releasing tension on the filter activation wire 242 allows the filter assembly 240 to move into the unexpanded configuration. In the expanded position, an outer diameter of the filter frame 240b around the central portion 240g and an outer diameter of the proximal portion 240f of the filter membrane 240a correspond to an inner diameter of an artery or vessel to ensure that any embolic material is captured by the filter assembly 240. In addition, the filter membrane 240a and the filter frame 240b allow blood/fluid to flow therethrough.

According to some implementations, the filter membrane 240a comprises a biocompatible, elastic polymer sheet (e.g., polyurethane) that defines an array of openings. In certain implementations, the openings are 40 micrometers in diameter, which allows blood to flow through but captures small particulates. And, in some implementations, the openings are formed by laser drilling. In addition, in various implementations, the filter frame 240b comprises a biocompatible, expandable structure that defines a plurality of openings. The openings of the filter frame 240b are larger than the openings defined by the filter membrane 240a. The filter frame 240b, according to some implementations, includes a material having memory properties, such as a braided nitinol structure or a laser cut nitinol tube structure. Other suitable biocompatible materials include titanium and titanium alloys, stainless steel, platinum, gold, or other metals, as well as ceramics or polymers. In some implementations, the filter frame 240b has a memory of the unexpanded configuration such that when tension on the filter activation wire 242 is released, the filter frame 240 returns toward its unexpanded configuration, capturing any embolic materials that have been captured within the filter assembly 240.

Figure 10A:
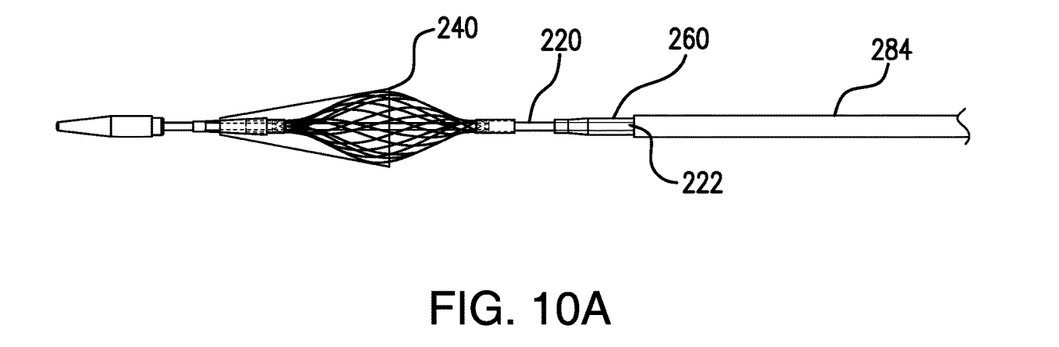
FIGS. 10A and 10B illustrate a side view of the catheter in FIG. 1 with the sheath exposing a portion of the expandable balloon and with the balloon fully expanded, respectively.
Figure 10B:
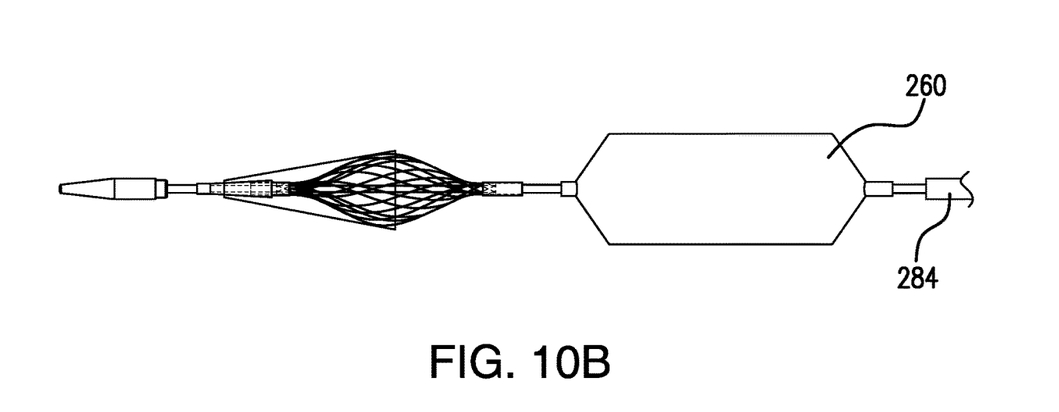

As shown in FIGS. 10A and 10B, an expandable balloon 260 is disposed between the proximal end 240d of the filter frame 240b and the proximal end of the distal portion 220b of the catheter 220. Air and/or fluid is provided to the balloon 260 for inflation via the balloon inflation lumens 224a, 224b defined by the proximal portion 220a and distal portion 220b of the catheter 220. In some implementations, a tube, such as a hypotube, is disposed within the balloon inflation lumens 224a, 224b for delivering the air/fluid to the balloon 260. A distal balloon inflation port (not shown) is defined by the distal portion 220b of the catheter 220 and extends between the balloon inflation lumen 224b and a portion of the external surface of the distal portion 220b that is in fluid communication with an inside of the balloon 260. The balloon 260 can be any impermeable, flexible membrane defining a chamber that is expandable by the introduction of fluid into the chamber.

As shown in FIGS. 10A and 10B, a movable sheath 284 can extend over the balloon 260 and filter assembly 240. Exemplary sheaths include a wire, coiled wire, polymer filament, or polymer braid sheath. For example, in some implementations, the sheath 284 comprises an inner polymer layer (e.g., PTFE composite) to reduce friction with components disposed radially within the sheath 284, a structural sheath layer (e.g., a wire, coiled wire, polymer filament, or polymer braid sheath layer (e.g., a braided stainless steel sheath layer)) to maintain the radial strength of the sheath 284, and an outer polymer layer (e.g., nylon) to protect the structural sheath layer. In addition, the sheath 284 is a 6F sheath/8F guide compatible sheath, according to one implementation.

Figure 12:
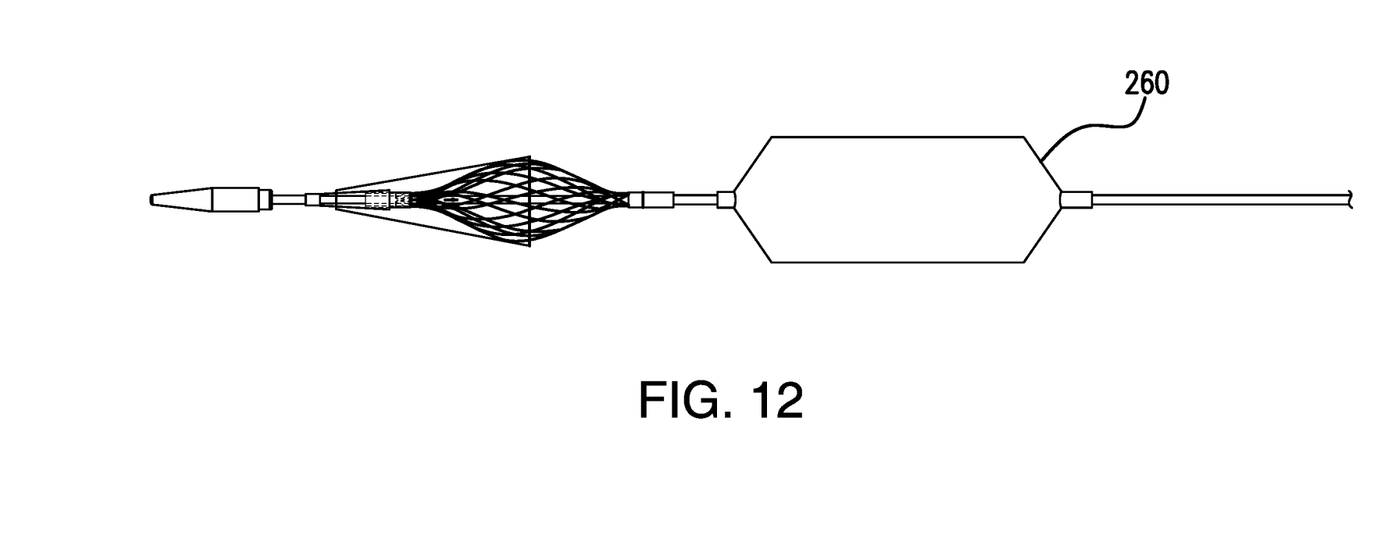
FIG. 12 is a side view of an implementation of the percutaneous transluminal angioplasty device without a sheath covering the balloon, with the balloon in the inflated state.

By disposing the sheath 284 over the therapeutic agent coated balloon 260 while introducing the balloon 260 into the body and routing the balloon 260 and filter assembly 240 through the body to the target site, the sheath 284 prevents loss of the therapeutic agent from the outer surface of the balloon 260 (e.g., by blood or other fluid(s) flowing past the balloon 260 or by other obstructions that may degrade or disturb the therapeutic agent). However, in some implementations, the sheath 284 does not extend over the filter assembly 240, and in other implementations, the sheath 284 extends over a portion of the filter assembly 240. Some implementations, such as the one shown in FIG. 12, do not include a sheath at all.

In some implementations, the therapeutic agent is an anti-stenotic therapeutic agent, such as Sirolimus (rapamycin) or Paclitaxel (taxol). Other examples of anti-stenotic therapeutic agents include heparin, other taxanes, tacrolimus, actinomycin D, angiopeptin, vassenoids, flavoperidol, estrogen, halofuginone, matrix metallopreteinase inhibitors, and interferons. However, in other implementations, the therapeutic agent comprises any therapeutic agent for delivery to an interior wall of a vessel. Examples of classes of therapeutic agents that can be included in the devices described herein depend on the specific disease being treated and the physical properties of the agent, which include, for example, pro- or anti-proliferative, anti-inflammatory, antimitotic, anti-platelet, anticoagulant, antifibrin, antithrombin, cytostatic, antibiotic, anti-enzymatic, anti-metabolic, angiogenic, cytoprotective, angiotensin converting enzyme (ACE) inhibiting, angiotensin II receptor antagonizing and/or cardioprotective agents.

Examples of antiproliferative drugs include, without limitation, actinomycins, taxol, docetaxel, paclitaxel, sirolimus (rapamycin), biolimus A9 (Biosensors International, Singapore), deforolimus, AP23572 (Ariad Pharmaceuticals), tacrolimus, temsirolimus, pimecrolimus, zotarolimus (ABT-578), 40-O-(2-hydroxy)ethyl-rapamycin (everolimus), 40-O-(3-hydroxypropyl)rapamycin (a structural derivative of rapamycin), 40-O-[2-(2-hydroxy)ethoxy]ethyl-rapamycin (a structural derivative of rapamycin), 40-O-tetrazole-rapamycin (a structural derivative of rapamycin), 40-O-tetrazolylrapamycin, 40-epi-(N-1-tetrazole)-rapamycin, and pirfenidone.

Examples of anti-inflammatory drugs include both steroidal and non-steroidal (NSAID) anti-inflammatories such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone dipropionate, dexamethasone acetate, dexmethasone phosphate, momentasone, cortisone, cortisone acetate, hydrocortisone, prednisone, prednisone acetate, betamethasone, betamethasone acetate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus and pimecrolimus.

Examples of anti-platelet, anticoagulant, antifibrin, and antithrombin drugs include, without limitation, heparin, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as ANGIOMAX® (bivalirudin, from Biogen), calcium channel blockers such as nifedipine, colchicine, fish oil (omega 3-fatty acid), histamine antagonists, lovastatin, monoclonal antibodies such as those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic and 4-amino-2,2,6,6-tetramethylpiperidine-1-oxyl (4-amino-TEMPO).

Examples of cytostatic drugs include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Examples of ACE inhibitors include, without limitation, quinapril, perindopril, ramipril, captopril, benazepril, trandolapril, fosinopril, lisinopril, moexipril and enalapril. Examples of angiotensin II receptor antagonists include, without limitation, irbesartan and losartan.

Therapeutic agents can be formulated as solid formulations, gels, or liquids suitable for administration using a therapeutic agent-coated balloon catheter. Such formulations are known in the art.

In some embodiments, the formulation can be a coating comprising a therapeutic agent formed on an outer surface of an expandable balloon. The coating can be formed by spraying, dipping, pouring, pumping, brushing, wiping, vacuum deposition, vapor deposition, plasma deposition, electrostatic deposition, ultrasonic deposition, epitaxial growth, electrochemical deposition or any other method known to those skilled in the art.

The coating can comprise one or more therapeutic agents and optionally one or more excipients and/or additives as described above. For example, the coating can include a biocompatible polymer. Suitable polymers can include both biostable and biodegradable polymers, such as microcrystalline cellulose, hydroxypropyl cellulose, hydroxypropyl methylcellulose, polyalkylene oxides such as polyethylene oxide (PEG), polyanhydrides, poly(ester anhydrides), polyhydroxy acids such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

The coating can comprise rate-controlling excipients, including hydrophobic materials, including acceptable fats and fatty substances (e.g., fatty alcohols, such as lauryl, myristyl stearyl, cetyl or cetostearyl alcohol, fatty acids and derivatives, including, but not limited to, fatty acid esters, fatty acid glycerides (mono-, di- and tri-glycerides), and hydrogenated fats), waxes and wax-like substances (e.g., natural or synthetic waxes, hydrocarbons, and normal waxes, including beeswax, glycowax, castor wax, carnauba wax, paraffins and candelilla wax), ion-exchange resins, water-insoluble proteins (e.g., zein), wicking agents (e.g., starch derivatives such as waxy maltodextrin and drum dried corn starch, cellulose derivatives such as hydroxypropylmethyl cellulose, hydroxypropyl cellulose, methyl cellulose, and carboxymethyl cellulose, alginic acid, lactose, dextrose, mannitol and talc), and surfactants.

If desired, one or more barrier layers can be placed over the coating to prevent dissolution of the therapeutic agent layer prior to positioning of the catheter where administration of the therapeutic agent is intended.

Figure 6:
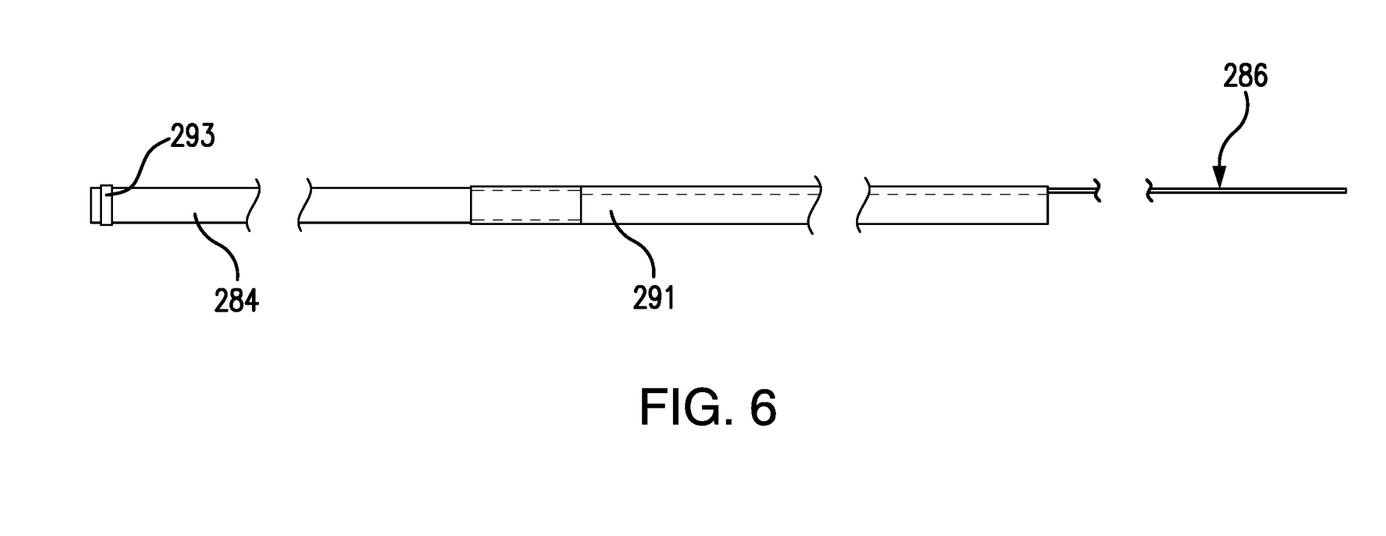
FIG. 6 illustrates a side view of portions of the sheath according to one implementation.

Furthermore, in the implementation shown in FIG. 6, the sheath 284 includes a radio-opaque marker 293 around a portion of the sheath 284 to assist in verifying proper placement of the sheath within the vessel before retracting the sheath 284 to expose the filter 240 and balloon 260. However, in other implementations, the sheath 284 may not include the radio-opaque marker 293. In addition, in some implementations, the sheath 284 may be tapered from its distal end toward its proximal end, wherein the distal end of the sheath 284 has a larger diameter than the proximal end of the sheath 284.

Figure 8:
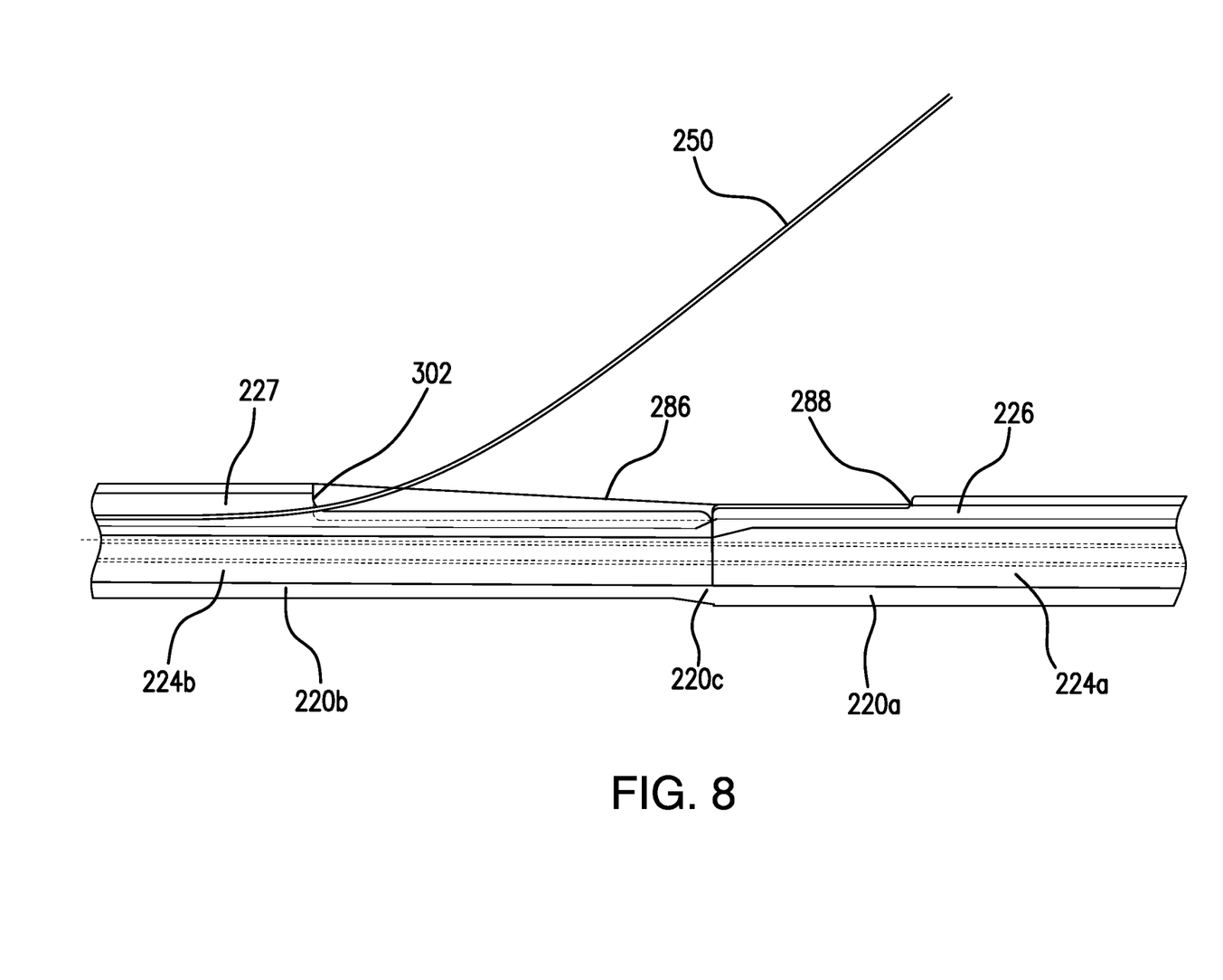
FIG. 8 illustrates a cross sectional view of the catheter shown in FIG. 1 as taken along the longitudinal axis A-A.

As shown in FIG. 8, which is a longitudinal cross-sectional view of the mid portion 220c of catheter, a sheath wire exit port 288 is defined between an external surface of the proximal portion 220a of the catheter 220 and the sheath wire lumen 226, and a sheath wire 286 extends between the sheath wire lumen 226 and the sheath 284 via the sheath wire exit port 288 (sheath 284 not shown in FIG. 8). In one implementation, the sheath wire exit port 288 is defined adjacent a distal end of the proximal portion 220a of the catheter 220. A distal end of the sheath wire 286 extends over the external surface of the distal portion 220b of the catheter to be coupledcoupled to the sheath 284. In some implementations, the sheath wire 286 is coupled to the sheath 284 by embedding the distal end of the sheath wire 286 between the braided structural layer and the outer polymer layer.

In some implementations, such as the one shown in FIG. 1, the sheath 284 does not extend over the entire length of the catheter. By disposing the sheath wire 286 within the proximal portion 220a of the catheter 220, the physician is able to stabilize (e.g., hold steady) the catheter 220 while the sheath 284 is moved axially proximal to the balloon 260, which reduces or prevents movement of the distal portion 220*b* of the catheter 220 and unintentional axial movement of the balloon relative to the target location during deployment of the balloon. In known devices, the sheath is not coupled to a sheath wire, and the sheath extends proximally over the entire length of the catheter. Thus, there is no space available on the catheter to hold the catheter steady during sheath deployment. Known devices do not include a sheath wire.

Figure 9A:
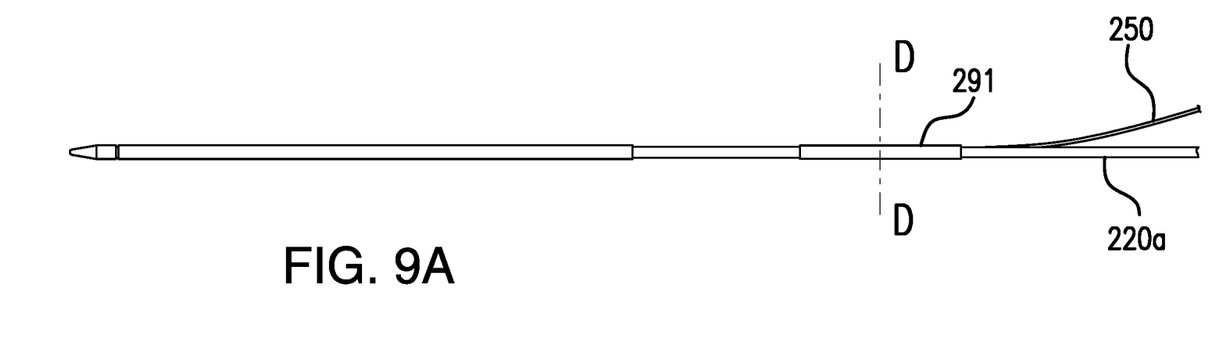
FIG. 9A illustrates a side view of the catheter in FIG. 6 having a sleeve, according to one implementation.
Figure 9B:
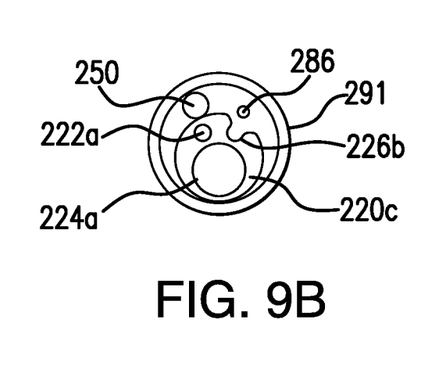
FIG. 9B illustrates a cross sectional view of the catheter and sleeve in FIG. 9A as taken through the D-D line.

In the implementation shown in FIG. 1, a portion of the sheath wire 286 extending between the sheath wire exit port 288 and the sheath 284 is exposed. However, in some implementations, such as is shown in FIGS. 6 and 9A and 9B, a sleeve 291 (e.g., a polymer sleeve) is disposed at least partially around the exposed portion of the sheath wire 286 and the mid portion 220*c* of the catheter. At least a portion of the exterior surface of mid portion 220*c* defines a recessed, axially extending groove 226*b* that is in communication with the sheath wire lumen 226 defined by the proximal portion 220*a*. The sheath wire 286 is radially movable in and out of the groove 226*b*, as seen in FIG. 9B. In the implementation shown, guidewire 250 is routed through a proximal end of the sleeve 291 toward the guidewire lumen 227 defined by the distal portion 220*b* of the catheter 220. In the implementation shown in FIGS. 6 and 9A, the sheath 284 and the sleeve 291 are coupled together. However, in other implementations, the sheath 284 and sleeve 291 are separately formed and disposed axially adjacent each other.

In the implementation shown in FIGS. 1 and 8, a proximal end of the distal portion 220*b* of the catheter 220 defines a guidewire port 302 that extends between the guidewire lumen 227 and an external surface of the catheter 220. The opening of the guidewire port 302 defined by the external surface of the catheter 220 is proximal to guidewire lumen 227 to facilitate rapid exchange of the guidewire 250. In the implementation shown, the guidewire port 302 is defined by the opening of the guidewire lumen 227 at the proximal end of the distal portion 220*b*. A proximal portion of the guidewire 250 extends out of the distal portion 220*b* of catheter 220 proximally of the sheath 284 via the guidewire port 302. The guidewire 250 according to some implementations has a diameter of between 0.010 inches and 0.038 inches (e.g., 0.014 inches). In other implementations, the guidewire port includes a first opening and a second opening. The first opening of the guidewire port is defined by the exterior surface of the catheter that is radially spaced apart from the guidewire lumen 227, and the second opening of the guidewire port is defined by an interior surface of the lumen 226 and is distally spaced apart from the first opening along the longitudinal axis of the guidewire lumen 227. That is, in various implementations, the guidewire port extends through the catheter 220 from a first opening towards a second opening defined by a lumen that is distally spaced from the first opening.

Figure 7A:
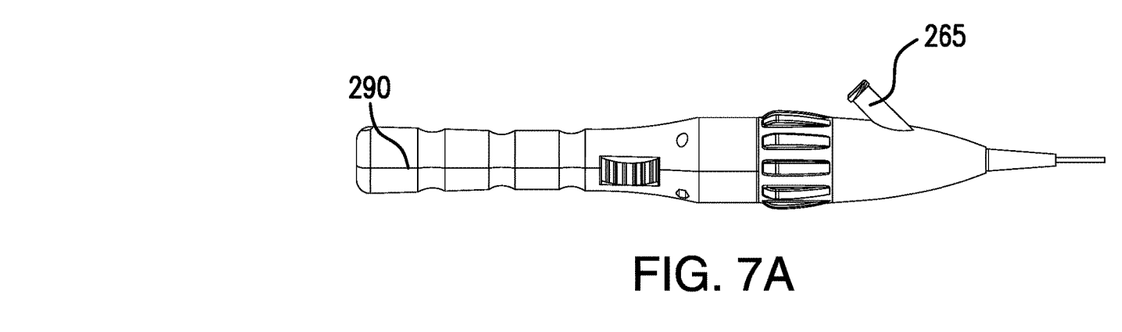
FIGS. 7A-7C illustrate a side view, partial cross sectional view, and an exploded view, respectively, of a handle according to one implementation.
Figure 7B:
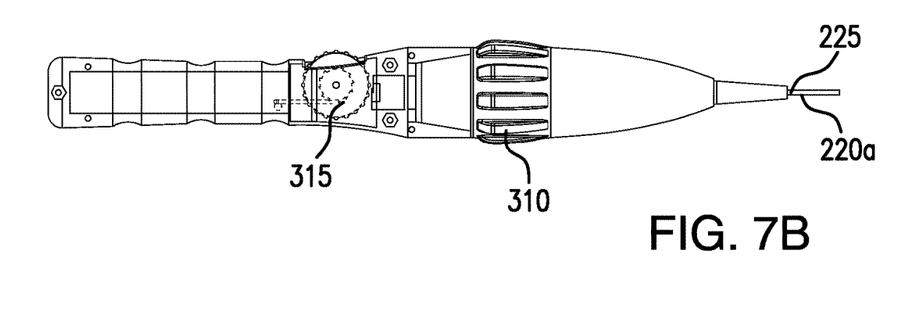
Figure 7C:
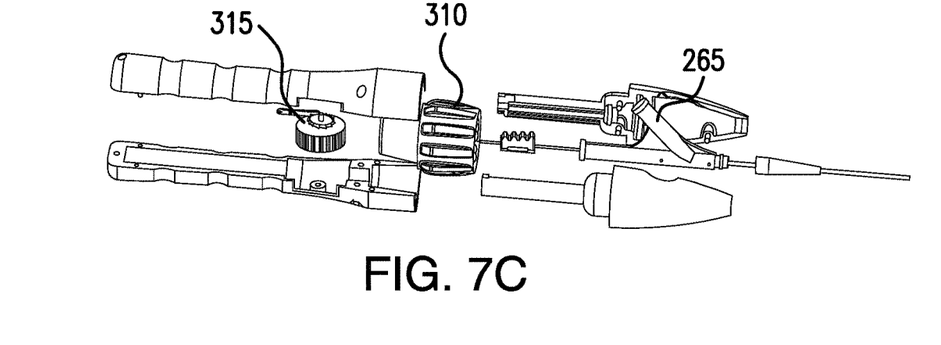

As shown in FIGS. 7A-7C, the device 200 further includes a handle 290 coupled to the proximal end 225 of the proximal portion 220*a* of the catheter 220. In some implementations, the handle 290 includes controls (e.g., buttons, knobs, etc.) that are coupled to one or more of the filter activation wire 242, the sheath wire 286, and/or the guidewire 250 to allow the user to actuate the filter 240, the sheath 284, and/or the guide wire 250. In the implementation shown in FIGS. 7A-7C, knobs 310, 315 are disposed on the handle 290 and are coupled to the filter activation wire 242 and the sheath wire 286, respectively. Actuation of the knobs 310, 315 in one direction causes the respective wires to be tensioned proximally, and actuation of the knobs 310, 315 in the opposite direction releases tension on the wires. In addition, as shown in FIG. 7A, the handle 290 defines a proximal balloon inflation port 265 that is in fluid communication with the balloon inflation lumens 224*a*, 224*b* and the balloon 260 to provide air/fluid to the balloon 260 for expansion.

As will be readily appreciated by those of skill in the art, various implementations of the percutaneous transluminal angioplasty device 200 and its corresponding components are formed from one or more biocompatible materials, such as cobalt chromium, titanium and titanium alloys, stainless steel, nitinol, platinum, gold, or other metals, as well as ceramics or polymers. In addition, in some implementations, the device 200 or portions thereof includes a coated or sheathed material. For example, the device 200 includes a bioresorbable material or has a bioresorbable coating or sheathing.

In use, the catheter 220 is advanced over guidewire 250 (e.g., under fluoroscopic guidance) to a target location/stenosis site within a blood vessel. FIGS. 10A and 10B illustrate how the device 200 is operated within the body according to one implementation. First, the sheath 284 is moved axially toward the proximal end 225 of the catheter 220 by pulling the sheath wire 286 proximally to expose the filter assembly 240. Then, the filter assembly 240 is deployed into the expanded configuration by tensioning the filter activation wire 242. Deploying the filter assembly 240 allows the filter assembly 240 to catch any embolic material that is dislodged during deployment of the balloon 260. One problem with conventional drug coated balloons is that the drug coating material may fragment off the balloon while it is being expanded within the treatment site resulting in a bolus of embolic particles carried along the artery toward more distal anatomy. Advantageously, the filter assembly 240 also catches any portion of the balloon coating that flakes off or becomes separated from the balloon 260 during expansion.

Next, in implementations that include sheath 284, the sheath is moved further axially toward the proximal end 225 to expose the therapeutic agent coated balloon 260. The distance the sheath is moved can be varied to expose either a portion of or the entirety of the balloon 260. Depending on the length the sheath 284 is retracted, the exposed, expanded length of the balloon can be varied. The portion of the balloon 260 remaining under the sheath 284 remains unexpanded, or at least expanded to a lesser diameter than the exposed portion of the balloon. This feature adds to the versatility of the device. For example, one catheter can be constructed with one long balloon (such as 200 mm long, for example). The exposed and expanded length of the balloon can be from anywhere from about 5 millimeters to 200 millimeters, including 5 millimeters, 25 millimeters, 50 millimeters, 75 millimeters, 100 millimeters, 125 millimeters, 150 millimeters, 175 millimeters, and 200 millimeters, depending on how far the sheath is retracted. Thus, a hospital could buy one catheter having a 200 millimeter balloon instead of multiple catheters having balloons with separate lengths, saving money and reducing inventory.

With the sheath 284 disposed proximally, the balloon 260 is inflated against an inner surface of the artery such that the vessel wall is expanded and the therapeutic agent on the surface of the balloon is delivered into the anastomotic lesion.

The balloon 260 is inflated (or deflated) via fluid/air provided to (or removed from) a central chamber of the balloon 260 via port 265. After the vessel is fully dilated, the balloon 260 is deflated, tension in the filter activation wire 242 is released, and the filter membrane 240a and the filter net 240b are collapsed by releasing the filter activation wire 242, which securely capture any embolic material captured by the filter assembly 240. The embolic material may include material from the vessel and fragments of the drug coating that separated from the balloon 260 during expansion. The blocked vessel is opened and blood flow is restored. The filter assembly 240 is then contracted by actuating the filter activation wire 242, and the device 200, which includes the deflated balloon 260 and the contracted filter assembly 240, are removed from the vessel. The catheter 220 is moved axially out of the body, which pulls the filter assembly 240 holding any captured embolic material and the unexpanded balloon 260 out of the body. Because the filter assembly 240 is able to capture and hold the embolic material upon release of the filter activation wire 242, it is not necessary to move the sheath 284 distally over the filter assembly 240 prior to removal of the device 200 from the body, which reduces the time required for the procedure.

As noted above, when the sheath wire 286 is tensioned to pull the sheath 284 away from the balloon 260, the proximal portion 220a and the distal portion 220b of the catheter 220 are able to be steadied by the physician (e.g., by holding the proximal portion 220a of the catheter) to prevent or reduce movement of the proximal portion 220a and the distal portion 220b relative to the sheath 284.

Having one device 200 that includes a filter, expandable therapeutic agent coated balloon, and a sheath activation wire reduces the time required to perform a vascular expansion procedure and reduces the potential for complications resulting from the procedure.

In addition, the various embodiments disclosed herein are adaptable for use in virtually any vessel where the capture emboli within the bloodstream is required for a therapeutic or diagnostic purpose. In addition, it is also anticipated that certain embodiments could be used for purposes other than medical, such as construction, manufacturing, and excavation, among others; accordingly, nothing herein is intended to limit application of the various embodiments to purely medical uses.

Accordingly, the subject matter described above is provided by way of illustration only and should not be construed as limiting. It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention, as defined by the following claims.

What is claimed is:

1. A percutaneous transluminal angioplasty device, comprising:
   a multi-lumen catheter having a proximal end and a distal end, the catheter defining a plurality of lumens, each lumen of the plurality of lumens extending through at least a portion of the catheter;
   a filter disposed adjacent the distal end of the catheter, the filter being movable between an unexpanded and an expanded configuration;
   an expandable balloon disposed between the filter and the distal end of the catheter, wherein the expandable balloon has an outer surface, and at least a portion of the outer surface comprises a therapeutic agent;
   a movable sheath extending over at least a portion of the expandable balloon in an unexpanded configuration of the expandable balloon;
   a sheath wire coupled to the movable sheath, the sheath wire extending through a first lumen of the plurality of lumens;
   a filter activation wire coupled to the filter, the filter activation wire extending through a second lumen of the plurality of lumens; and
   a handle coupled to a proximal end of the catheter;
   wherein the handle includes a first actuation knob coupled to the filter activation wire and a second actuation knob coupled to the sheath wire, the first actuation knob being manipulatable to expand and contract the filter via the filter activation wire, and the second actuation knob being manipulatable to axially move the sheath via the sheath wire.

2. The percutaneous transluminal angioplasty device of claim 1, wherein the therapeutic agent is an anti-stenotic therapeutic agent.

3. The percutaneous transluminal angioplasty device of claim 2, wherein the anti-stenotic therapeutic agent is selected from the group consisting of Sirolimus and Paclitaxel.

4. The percutaneous transluminal angioplasty device of claim 1, wherein the sheath wire is moved axially to translate the sheath axially, and wherein the axial movement of the sheath wire translates the sheath in the same direction as the axial movement of the sheath wire.

5. The percutaneous transluminal angioplasty device of claim 1, wherein the filter comprises a filter frame and a filter membrane, the filter frame has a distal end and a proximal end, the proximal end of the filter frame being fixedly coupled to the catheter, and the distal end of the filter frame being slidably coupled to the catheter, the filter membrane has a distal end and proximal end, and the distal end of the filter membrane is fixedly coupled to the catheter distally of the proximal end of the filter membrane and the distal end of the filter frame, and the proximal end of the filter membrane is fixedly coupled to a portion of the filter frame, and the distal end of the filter activation wire is coupled to the distal end of the filter frame, wherein tensioning the filter activation wire in a proximal direction urges the distal end of the filter frame in axial proximal direction from an unexpanded configuration to an expanded configuration.

6. The percutaneous transluminal angioplasty device of claim 1, wherein a third lumen of the plurality of lumens is a balloon inflation lumen, the catheter further defining an inflation port between an external surface of the catheter and the.

7. The percutaneous transluminal angioplasty device of claim 1, wherein the catheter defines a guidewire port, the guidewire port having a first opening defined by a selected lumen of the plurality of lumens and a second opening defined by an exterior surface of the catheter, wherein the first opening of the guidewire port is disposed distally relative to the second opening.

8. The percutaneous transluminal angioplasty device of claim 7, wherein a guide wire is disposed within at least a portion of the selected lumen that defines the first opening of the guidewire port.

9. The percutaneous transluminal angioplasty device of claim 1, wherein at least a portion of the filter has a radius in the expanded configuration that corresponds to an inner diameter of a blood vessel into which the filter is disposed.

10. The percutaneous transluminal angioplasty device of claim 1, wherein the catheter comprises a proximal portion and a distal portion, the proximal portion being disposed adjacent a proximal end of the catheter and the distal portion being disposed adjacent a distal end of the catheter, wherein the proximal portion of the catheter defines a sheath wire lumen, a proximal filter activation wire lumen, and a proximal balloon inflation lumen, and the distal portion of the catheter defines a guidewire lumen, a distal filter activation wire lumen, and a distal balloon inflation lumen.

11. The percutaneous transluminal angioplasty device of claim 10, wherein the proximal balloon inflation lumen and the distal balloon inflation lumen are axially aligned.

12. The percutaneous transluminal angioplasty device of claim 10, wherein the proximal filter activation wire lumen and the distal filter activation wire lumen are axially aligned.

13. The percutaneous transluminal angioplasty device of claim 11, wherein the sheath wire lumen and the guidewire lumen are axially aligned.

14. A method of treating an artery comprising:
routing a percutaneous transluminal angioplasty device through a body to a site of a vascular stenosis, the device comprising a handle comprising first and second actuation knobs, a multi-lumen catheter, a filter, an expandable balloon comprising a therapeutic agent disposed on at least a portion of an outer surface of the expandable balloon, and a axially movable sheath disposed over at least a portion of the expandable balloon;
disposing a distal end of the catheter downstream of the vascular stenosis such that the balloon is disposed radially inward of the vascular stenosis and the filter is disposed downstream of the vascular stenosis;
tensioning an activation wire using the first actuation knob, thereby deploying the filter downstream of the vascular stenosis;
tensioning a sheath wire using the second actuation knob to axially move the sheath proximally, thereby exposing at least a portion of the expandable balloon;
inflating the balloon to push the outer surface of the balloon against the vascular stenosis and deliver the therapeutic agent to the vascular stenosis;
deflating the balloon;
contracting the filter; and
removing the catheter from the body.

15. The method of claim 14, wherein inflating the expandable balloon further comprises expanding an exposed portion of the balloon to a greater diameter than a portion of the balloon remaining under the axially movable sheath.

16. The method of claim 14, wherein the method further comprises axially moving the sheath proximally to expose the entire balloon prior to inflating the expandable balloon.

17. A percutaneous transluminal angioplasty device, comprising:
a multi-lumen catheter having a proximal end and a distal end, the catheter defining a plurality of lumens, each lumen of the plurality of lumens extending through at least a portion of the catheter;
an expandable balloon disposed on the catheter, wherein the expandable balloon has an outer surface, and at least a portion of the outer surface comprises a therapeutic agent;
a movable sheath extending over at least a portion of the expandable balloon in an unexpanded configuration of the expandable balloon;
a sheath wire coupled to the movable sheath, the sheath wire extending through a first lumen of the plurality of lumens;
a filter disposed adjacent the distal end of the catheter, the filter being movable between an unexpanded and an expanded configuration, and the expandable balloon being disposed axially proximal of the filter;
a filter activation wire is disposed within a second lumen of the plurality of lumens, and a distal end of the filter activation wire is coupled to the filter; and
a handle coupled to a proximal end of the catheter;
wherein the handle includes a sheath actuation knob that is coupled to the sheath wire, the sheath actuation knob being manipulatable to axially move the sheath via the sheath wire;
wherein the handle includes a filter actuation knob that is coupled to the filter activation wire, the filter actuation knob being manipulatable to expand and contract the filter via the filter wire.

18. The percutaneous transluminal angioplasty device of claim 17, wherein the therapeutic agent is an anti-stenotic therapeutic agent.

19. The percutaneous transluminal angioplasty device of claim 18, wherein the anti-stenotic therapeutic agent is selected from the group consisting of Sirolimus and Paclitaxel.

20. The percutaneous transluminal angioplasty device of claim 17, wherein the sheath wire is moved axially to translate the sheath axially, and wherein the axial movement of the sheath wire translates the sheath in the same direction as the axial movement of the sheath wire.

21. The percutaneous transluminal angioplasty device of claim 17, wherein the filter comprises a filter frame and a filter membrane, the filter frame has a distal end and a proximal end, the proximal end of the filter frame being fixedly coupled to the catheter, and the distal end of the filter frame being slidably coupled to the catheter, the filter membrane has a distal end and proximal end, and the distal end of the filter membrane is fixedly coupled to the catheter distally of the proximal end of the filter membrane and the distal end of the filter frame, and the proximal end of the filter membrane is fixedly coupled to a portion of the filter frame, and the distal end of the filter activation wire is coupled to the distal end of the filter frame, wherein tensioning the filter activation wire in a proximal direction urges the distal end of the filter frame in axial proximal direction from an unexpanded configuration to an expanded configuration.

22. The percutaneous transluminal angioplasty device of claim 17, wherein the plurality of lumens comprises a balloon inflation lumen, the catheter further defining an inflation port between an external surface of the catheter and the balloon inflation lumen.

23. The percutaneous transluminal angioplasty device of claim 17, wherein the catheter defines a guidewire port, the guidewire port having a first opening defined by a selected lumen of the plurality of lumens and a second opening defined by an exterior surface of the catheter, wherein the first opening of the guidewire port is disposed distally relative to the second opening.

24. The percutaneous transluminal angioplasty device of claim 23, wherein a guide wire is disposed within at least a portion of selected lumen that defines the first opening of the guidewire port.

25. The percutaneous transluminal angioplasty device of claim 17, wherein at least a portion of the filter has a radius in the expanded configuration that corresponds to an inner diameter of a blood vessel into which the filter is disposed.

26. The percutaneous transluminal angioplasty device of claim 17, wherein the catheter comprises a proximal portion and a distal portion, the proximal portion being disposed adjacent a proximal end of the catheter and the distal portion being disposed adjacent a distal end of the catheter, wherein the proximal portion of the catheter defines a sheath wire lumen, a proximal filter activation wire lumen, and a proximal balloon inflation lumen, and the distal portion of the catheter defines a guidewire lumen, a distal filter activation wire lumen, and a distal balloon inflation lumen.

27. The percutaneous transluminal angioplasty device of claim 26, wherein the proximal balloon inflation lumen and the distal balloon inflation lumen are axially aligned.

28. The percutaneous transluminal angioplasty device of claim 26, wherein the proximal filter activation wire lumen and the distal filter activation wire lumen are axially aligned.

29. The percutaneous transluminal angioplasty device of claim 27, wherein the sheath wire lumen and the guidewire lumen are axially aligned.

\* \* \* \* \*

UNITED STATES PATENT AND TRADEMARK OFFICE
CERTIFICATE OF CORRECTION

PATENT NO. : 10,849,730 B2
APPLICATION NO. : 15/840294
DATED : December 1, 2020
INVENTOR(S) : Ravish Sachar et al.

Page 1 of 1

It is certified that error appears in the above-identified patent and that said Letters Patent is hereby corrected as shown below:

In the Claims

Claim 6, Column 14, Line 50, "the" should read --the balloon inflation lumen--.

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*